(12) United States Patent
Nishimura et al.

(10) Patent No.: US 11,435,570 B2
(45) Date of Patent: Sep. 6, 2022

(54) IMAGE PICKUP APPARATUS FOR ENDOSCOPE, ENDOSCOPE, AND MANUFACTURING METHOD OF IMAGE PICKUP APPARATUS FOR ENDOSCOPE

(71) Applicant: OLYMPUS CORPORATION, Tokyo (JP)

(72) Inventors: Yoshiro Nishimura, Okaya (JP); Hiroshi Iwaisako, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 109 days.

(21) Appl. No.: 17/078,794

(22) Filed: Oct. 23, 2020

(65) Prior Publication Data
US 2021/0096355 A1   Apr. 1, 2021

Related U.S. Application Data

(63) Continuation of application No. PCT/JP2018/016643, filed on Apr. 24, 2018.

(51) Int. Cl.
*G02B 23/24* (2006.01)
*G02B 23/26* (2006.01)
(Continued)

(52) U.S. Cl.
CPC ........ *G02B 23/2484* (2013.01); *A61B 1/0051* (2013.01); *A61B 1/051* (2013.01);
(Continued)

(58) Field of Classification Search
CPC .. G02B 23/2484; G02B 23/26; H04N 5/2253; H04N 5/2254; H04N 7/183;
(Continued)

(56) References Cited

U.S. PATENT DOCUMENTS

2010/0074581 A1  3/2010 Tanobe et al.
2011/0211053 A1* 9/2011 Nakayama ........... H04N 5/2253
                                                    348/294
(Continued)

FOREIGN PATENT DOCUMENTS

EP    2624304 A1    8/2013
EP    2947486 A1    11/2015
(Continued)

OTHER PUBLICATIONS

International Search Report dated Jul. 17, 2018 received in PCT/JP2018/016643.

*Primary Examiner* — Tat C Chio
(74) *Attorney, Agent, or Firm* — Scully, Scott, Murphy & Presser, P.C.

(57) ABSTRACT

An image pickup apparatus for endoscope includes: an imager, an optical device, an optical module on which the optical device is mounted, an optical fiber optically coupled with the optical device, a ferrule having an insertion hole into which the optical fiber is inserted, and a wiring board including a first rigid board, a second rigid board and a flexible intermediate board. The ferrule is fixed to the second rigid board or a first principal surface of the optical module. A first side surface of the optical module is glued to the first rigid board, and the first principal surface is glued to the second rigid board.

12 Claims, 9 Drawing Sheets

(51) Int. Cl.
*H04N 5/225* (2006.01)
*H04N 7/18* (2006.01)
*A61B 1/05* (2006.01)
*A61B 1/005* (2006.01)
*G02B 23/02* (2006.01)
*A61B 1/00* (2006.01)

(52) U.S. Cl.
CPC ............. *G02B 23/02* (2013.01); *G02B 23/26* (2013.01); *H04N 5/2253* (2013.01); *H04N 5/2254* (2013.01); *H04N 7/183* (2013.01); *A61B 1/0011* (2013.01); *A61B 1/0017* (2013.01); *A61B 1/00105* (2013.01); *A61B 1/00117* (2013.01); *A61B 1/00126* (2013.01); *A61B 1/05* (2013.01); *H04N 2005/2255* (2013.01)

(58) Field of Classification Search
CPC ........ H04N 2005/2255; A61B 1/00105; A61B 1/0011; A61B 1/00117; A61B 1/00126; A61B 1/0017; A61B 1/05; A61B 1/051
See application file for complete search history.

(56) References Cited

U.S. PATENT DOCUMENTS

| | | |
|---|---|---|
| 2013/0182099 A1 | 7/2013 | Nakamura |
| 2015/0086162 A1* | 3/2015 | Miyahara ........... G02B 23/2446 385/33 |
| 2015/0188514 A1* | 7/2015 | Yamada ............... H03H 9/0547 310/370 |
| 2015/0318924 A1 | 11/2015 | Motohara |
| 2018/0008132 A1 | 1/2018 | Sakai et al. |

FOREIGN PATENT DOCUMENTS

| | | |
|---|---|---|
| JP | 2000-049439 A | 2/2000 |
| JP | 2012-079851 A | 4/2012 |
| JP | 2013-015859 A | 1/2013 |
| JP | 2014-137584 A | 7/2014 |
| WO | 2008-096716 A1 | 8/2008 |
| WO | 2012-043187 A1 | 5/2012 |
| WO | 2014-112461 A1 | 7/2014 |
| WO | 2016-151670 A1 | 9/2016 |

* cited by examiner

IMAGE PICKUP APPARATUS FOR ENDOSCOPE, ENDOSCOPE, AND MANUFACTURING METHOD OF IMAGE PICKUP APPARATUS FOR ENDOSCOPE

CROSS REFERENCE TO RELATED APPLICATION

This application is a continuation application of PCT/JP2018/016643 filed on Apr. 24, 2018, the entire contents of which are incorporated herein by this reference.

BACKGROUND OF THE INVENTION

1. Field of the Invention

The present invention relates to an image pickup apparatus for endoscope, an endoscope provided with the image pickup apparatus for endoscope, and a manufacturing method of the image pickup apparatus for endoscope.

2. Description of the Related Art

An endoscope has an image pickup device at a distal end portion of an elongated insertion portion. Recently, in order to display an image with a high quality, an image pickup device with a high pixel count has been considered. When an image pickup device with a high pixel count is used, an image signal amount transmitted from the image pickup device to a signal processing device (processor) increases. Therefore, in electrical signal transmission via a metal wire (a signal cable) by an electrical signal, it is necessary to increase a diameter of the metal wire or use a plurality of metal wires to transmit a required signal amount, and there is a possibility that the insertion portion becomes thick.

In order to reduce a diameter of the insertion portion to realize minimal invasiveness, optical signal transmission via a thin optical fiber by an optical signal instead of an electrical signal is preferred.

Japanese Patent Application Laid-Open Publication No. 2014-137584 discloses an image pickup apparatus that converts an electrical signal, which is outputted by an image pickup device, into an optical signal by an optical device and transmits the optical signal via an optical fiber. The optical device is mounted on a first surface of a flexible substrate, which has the first surface and a second surface that are orthogonal to each other, and a metal cable is connected to the second surface in parallel to an optical axis of the optical fiber.

However, it is not easy to bend the flexible substrate so as to be brought into a state in which the first and second surfaces are orthogonal.

Japanese Patent Application Laid-Open Publication No. 2013-15859 discloses a connector housing where a first substrate on which an optical device is mounted and a second substrate on which a semiconductor device is mounted are connected via a metal wire, and the first substrate is tilted at a predetermined angle relative to the second substrate.

SUMMARY OF THE INVENTION

An image pickup apparatus for endoscope of an embodiment of the present invention includes: an imager configured to output an image pickup signal; an optical device configured to convert the image pickup signal into an optical signal; an optical module on which the optical device is mounted, the optical module including a first principal surface, a second principal surface on an opposite side of the first principal surface, and a first side surface, an angle of the first side surface relative to the first principal surface being a predetermined angle; an optical fiber configured to transmit the optical signal and configured to be optically coupled with the optical device; a ferrule having an insertion hole into which the optical fiber is inserted; and a wiring board including a first rigid board, a second rigid board, and a flexible intermediate board connecting the first rigid board and the second rigid board. The ferrule is fixed to the second rigid board or the first principal surface of the optical module, and the first side surface of the optical module is glued to the first rigid board and the first principal surface is glued to the second rigid board.

An endoscope of the embodiment of the present invention includes an image pickup apparatus for endoscope. The image pickup apparatus for endoscope includes: an imager configured to output an image pickup signal; an optical device configured to convert the image pickup signal into an optical signal; an optical module on which the optical device is mounted, the optical module including a first principal surface, a second principal surface on an opposite side of the first principal surface, and a first side surface, an angle of the first side surface relative to the first principal surface being a predetermined angle; an optical fiber configured to transmit the optical signal and configured to be optically coupled with the optical device; a ferrule having an insertion hole into which the optical fiber is inserted; and a wiring board including a first rigid board, a second rigid board, and a flexible intermediate board connecting the first rigid board and the second rigid board. The ferrule is fixed to the second rigid board or the first principal surface of the optical module, and the first side surface of the optical module is glued to the first rigid board and the first principal surface is glued to the second rigid board.

A manufacturing method of an image pickup apparatus for endoscope of another embodiment of the present invention is a manufacturing method of an image pickup apparatus for endoscope, the image pickup apparatus for endoscope including: an imager configured to output an image pickup signal; an optical device configured to convert the image pickup signal into an optical signal; an optical module on which the optical device is mounted, the optical module including a first principal surface, a second principal surface on an opposite side of the first principal surface, and a first side surface, an angle of the first side surface relative to the first principal surface being a predetermined angle; an optical fiber configured to transmit the optical signal and configured to be optically coupled with the optical device; a ferrule having an insertion hole into which the optical fiber is inserted; and a wiring board including a first rigid board, a second rigid board, and a flexible intermediate board connecting the first rigid board and the second rigid board; the ferrule being fixed to the second rigid board or the first principal surface of the optical module; and the first side surface of the optical module being glued to the first rigid board, and the first principal surface being glued to the second rigid board. The method includes gluing the first principal surface of the optical module to the second rigid board; and bending the intermediate board and gluing the side surface of the optical module to the first rigid board.

DETAILED DESCRIPTION OF THE PREFERRED EMBODIMENTS

First Embodiment

Figure 1:
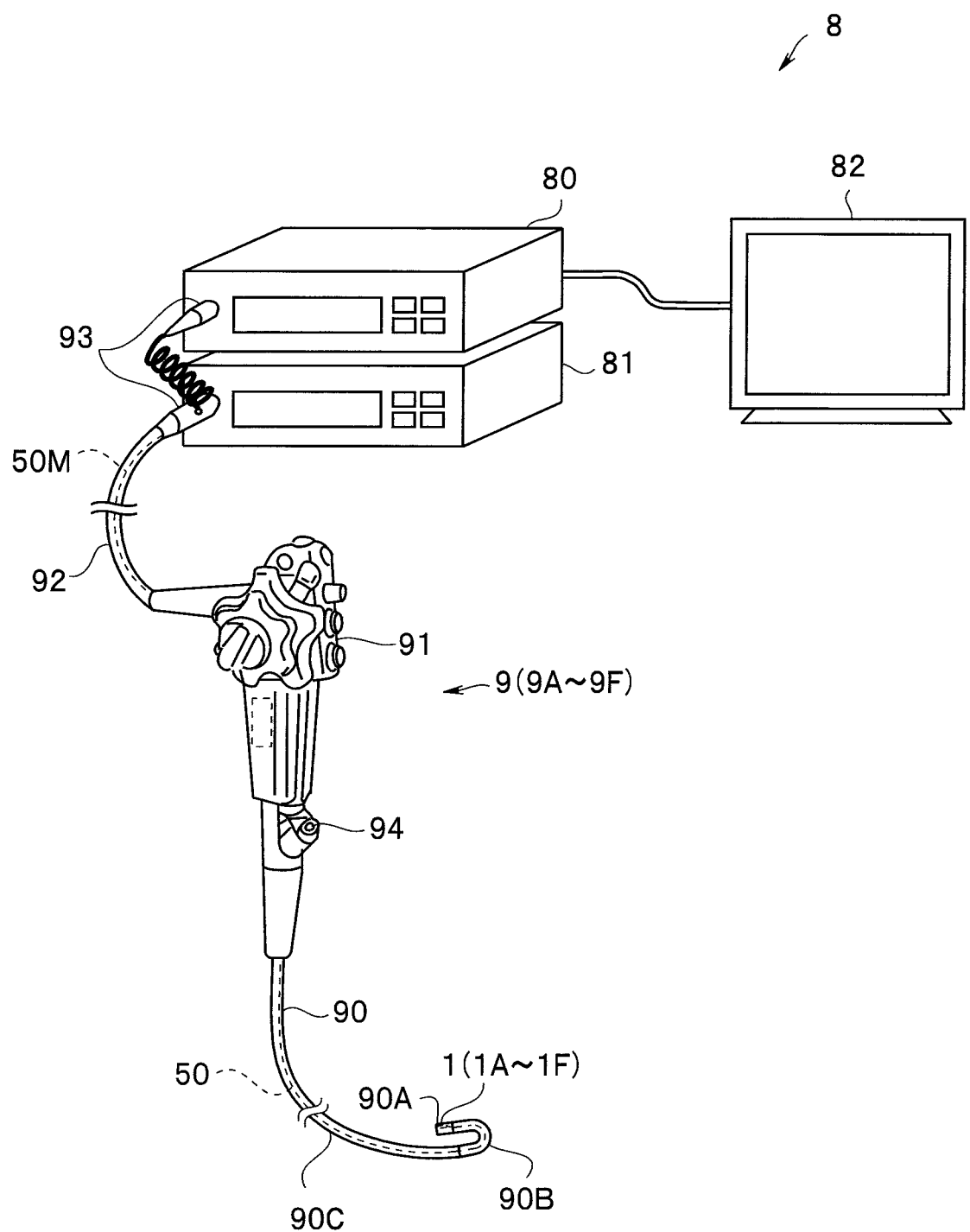
FIG. 1 is a configuration diagram of an endoscope system that includes an endoscope of a first embodiment.

As shown in FIG. 1, an endoscope system 8 that includes an endoscope 9 of the present embodiment is provided with the endoscope 9, a processor 80, a light source apparatus 81 and a monitor 82. For example, the endoscope 9 photographs an in-vivo image of a subject and outputs an image pickup signal by an insertion portion 90 being inserted into a body cavity of the subject.

On a proximal end portion of the insertion portion 90 of the endoscope 9, an operation portion 91 provided with various kinds of buttons for operating the endoscope 9 is continuously provided. On the operation portion 91, there is a treatment instrument insertion port 94 of a channel through which bio-forceps, an electrosurgical knife, a test probe and the like are inserted into a body cavity of a subject.

Figure 2:
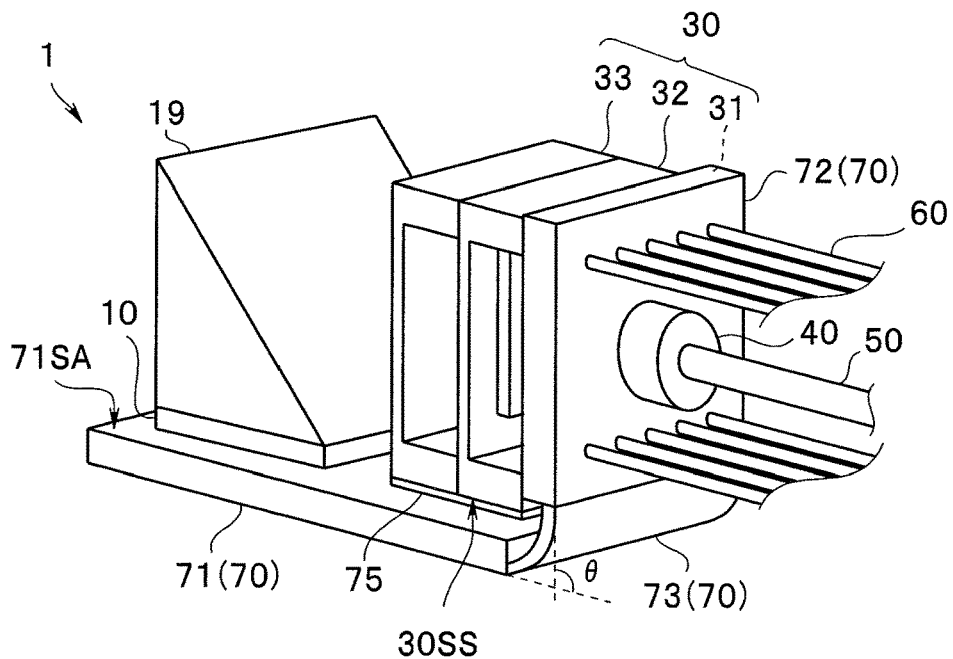
FIG. 2 is a perspective view of an image pickup apparatus of the first embodiment.
Figure 3:
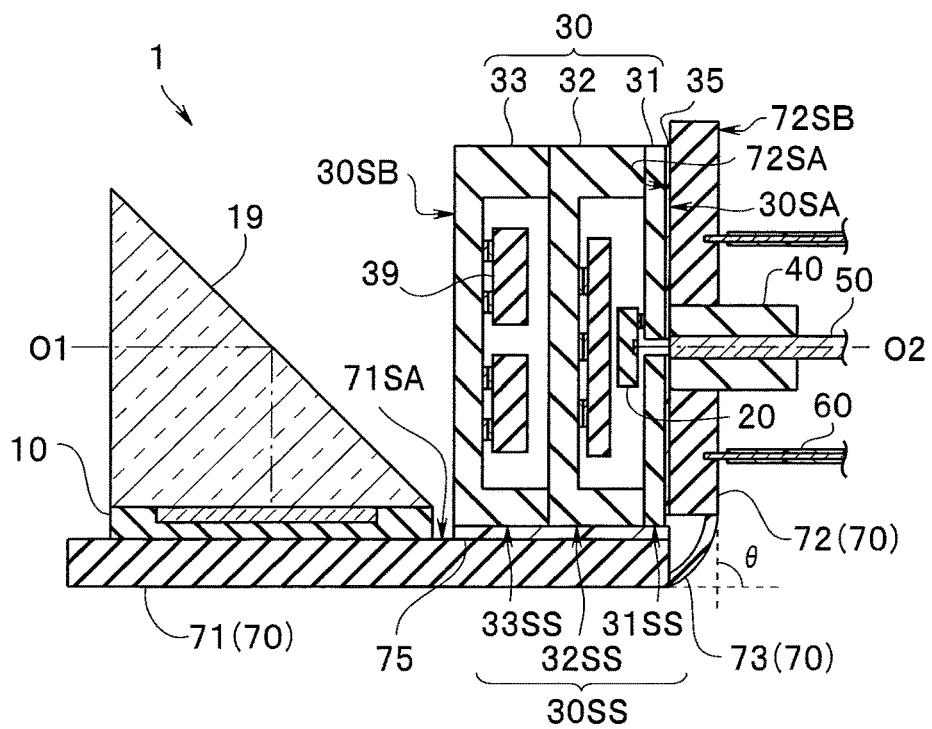
FIG. 3 is a sectional view of the image pickup apparatus of the first embodiment.

The insertion portion 90 is configured with a rigid distal end portion 90A where an image pickup apparatus for endoscope 1 (hereinafter referred to as an "image pickup apparatus"; see FIG. 2 and the like) is disposed, a bendable bending portion 90B continuously provided on a proximal end portion of the distal end portion 90A and a flexible portion 90C continuously provided on a proximal end portion of the bending portion 90B. The bending portion 90B bends by an operation of the operation portion 91.

A universal cord 92 extended from the operation portion 91 is connected to the processor 80 and the light source apparatus 81 via a connector 93. The processor 80 controls the whole endoscope system 8, and performs signal processing on an image pickup signal outputted by the image pickup apparatus 1, to output the image pickup signal as an image signal. The monitor 82 displays the image signal outputted by the processor 80.

The light source apparatus 81 has, for example, a white LED. Illumination light emitted by the light source apparatus 81 is guided to an illumination optical system of the distal end portion 90A via a light guide (not shown) inserted in the universal cord 92 and the insertion portion 90 to illuminate an object.

In the endoscope 9, the image pickup apparatus 1 of the distal end portion 90A converts an image pickup signal into an optical signal and then outputs the optical signal. The optical signal is transmitted to the operation portion 91 via a thin optical fiber 50 inserted in the insertion portion 90. Then, the optical signal is converted into an electrical signal again by an O/E type optical module (not shown) disposed on the operation portion 91, and is transmitted to the electrical connector 93 via a signal cable 50M which is a metal wire inserted in the universal cord 92.

In other words, an image pickup signal is transmitted through the optical fiber 50 in the insertion portion 90 with a thin diameter and is transmitted via the signal cable 50M, which is a metal wire thicker than the optical fiber 50, in the universal cord 92 which is not inserted into an inside of a body and the outer diameter of which is not restricted much.

Note that, if the O/E type optical module is arranged in the connector 93 or the processor 80, the optical fiber 50 is inserted in the universal cord 92.

<Configuration of Image Pickup Apparatus for Endoscope>

The image pickup apparatus for endoscope 1 of the present embodiment will be described, with reference to FIGS. 2 to 5.

Note that, in the description below, it should be noticed that the drawings are schematic, and a relationship between thickness and width of each portion, a thickness ratio among respective portions, and the like are different from actual ones, and, among the drawings, portions that are different in mutual dimensional relationship and ratio may be included. Further, a part of components may be neither shown nor given reference signs.

The image pickup apparatus 1 is provided with an imager 10 which is an image pickup portion, an optical device 20, an optical module 30 which is a fixed portion, a ferrule 40, the optical fiber 50, a cable 60 and a wiring board 70.

The imager 10 outputs an image pickup signal. The imager 10 is a CCD device or a CMOS device, and a light receiving portion 1 is formed on a light receiving surface 10SA. External electrodes 12 connected with the light receiving portion 11 are connected to bonded electrodes 13 on a back surface 10SB on an opposite side of the light receiving surface 10SA, via a through wire (not shown).

A right-angle prism 19 is disposed on the light receiving surface 10SA. In other words, the image pickup apparatus 1 is of a so-called horizontal type in which an optical axis O1 of an image pickup optical system not shown in FIGS. 2 to 5 (see FIG. 12) and the light receiving surface 10SA of the imager 10 are parallel to each other. A cover glass to protect the light receiving portion 11 may be glued on the light receiving surface 10SA, and the right-angle prism 19 may be disposed on the cover glass.

The optical device 20 converts an electrical signal outputted by the imager 10 into an optical signal. The optical device 20 is a VCSEL (vertical cavity surface emitting laser) having a light emitting portion 21 configured to output an optical signal. The optical device 20 is so ultra-compact that a size of a section orthogonal to an extension direction of the optical fiber 50 inserted in an insertion hole H40 of the ferrule 40, that is, an optical axis O2 which is a light emission direction of the optical device 20, that is, planar view dimensions are 250 μm×250 μm. The optical device 20 includes, on a light emission surface 20SA, the light emitting portion 21 with a diameter of 10 μm and two external terminals 22 with a diameter of 70 m that are connected to the light emitting portion.

The optical module 30 formed in a substantially rectangular parallelepiped shape generates an optical signal. The optical module 30 has a first principal surface 30SA, a second principal surface 30SB on an opposite side of the first principal surface 30SA, and a first side surface 30SS.

The optical device 20 is mounted in the optical module 30. Note that "being mounted" means not only being merely disposed but also being electrically connected.

Figure 5:
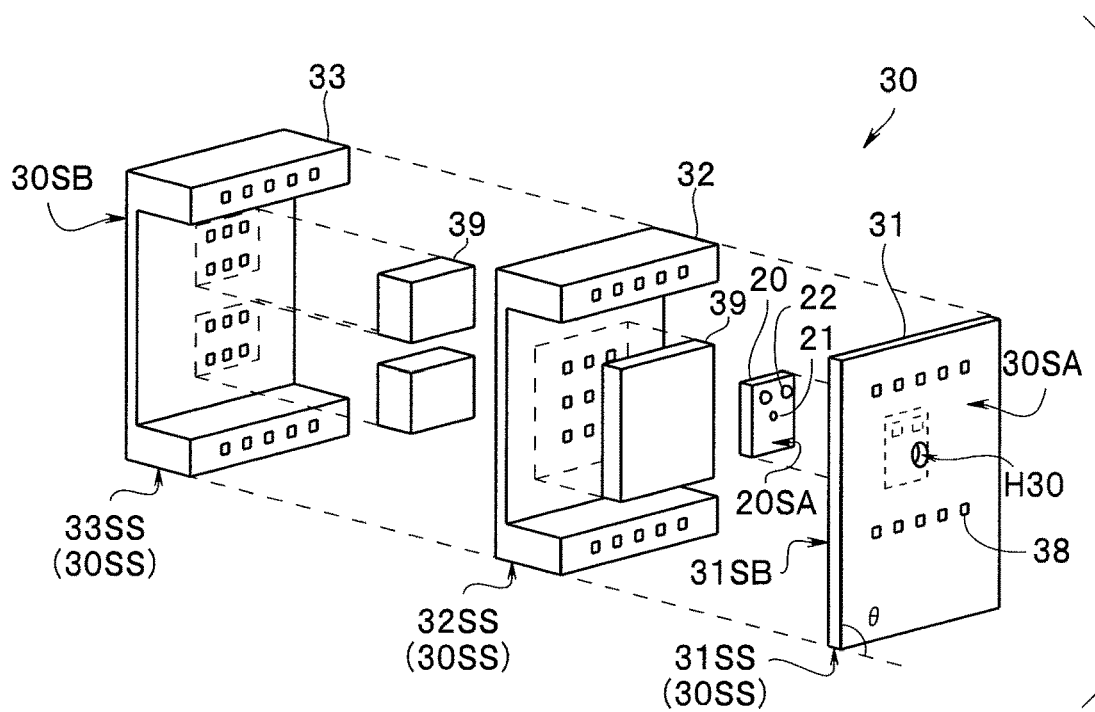
FIG. 5 is an exploded perspective view of an optical module of the image pickup apparatus of the first embodiment.

As shown in FIG. 5, the optical module 30 includes a first substrate 31, a second substrate 32, and a third substrate 33. The optical device 20 is mounted on the first substrate 31, and electronic parts 39 are mounted respectively on the second substrate 32 and the third substrate 33. The first substrate 31, the second substrate 32 and the third substrate 33 are electrically connected, for example, by solder bonding.

In other words, the optical module 30 is a three-dimensional wiring board on which the optical device 20 and the electronic parts 39 which are chip-shaped surface mount devices (SMDs) such as capacitors, inductors or signal processing ICs are mounted. In the image pickup apparatus 1, since the electronic parts 39 are mounted at places close to the optical device 20, wires between the optical device 20 and the electronic parts 39 are short. Therefore, the image pickup apparatus 1 is less susceptible to noise.

The first side surface 30SS of the optical module 30 is configured with a side surface 31SS of the first substrate 31, a side surface 32SS of the second substrate 32 and a side surface 33SS of the third substrate 33. In other words, the side surface 31SS, the side surface 32SS and the side surface 33SS are on the same plane.

The optical device 20 is mounted on a back surface 31SB on the opposite side of the first principal surface 30SA of the first substrate 31, and there is a first through hole H30 constituting an optical path, on the first substrate 31.

The optical fiber 50 transmits an optical signal. For example, the optical fiber 50 is configured with a core with a diameter of 50 μm configured to transmit an optical signal and a clad with a diameter of 125 μm that covers an external circumference of the core.

The ferrule 40 has the insertion hole H40 with a circular-shaped section orthogonal to the optical axis O2. A distal end portion of the optical fiber 50 is inserted in the insertion hole H40 and fixed with an adhesive. The optical fiber 50 inserted in the insertion hole H40 is optically coupled with the optical device 20.

The material of the ferrule 40 is a metal member such as stainless steel, ceramics, silicon, or glass. The outer surface shape of the ferrule 40 may be a prism, a substantial cylinder, a cone, or a polygonal prism.

The wiring board 70 has a first rigid board 71, a second rigid board 72 and an intermediate board 73 which is a connection portion having a wire electrically connecting the first rigid board 71 and the second rigid board 72. The first rigid board 71 has a principal surface 71SA and a back surface 71SB on an opposite side of the principal surface 71SA. The second rigid board 72 has a principal surface 72SA and a back surface 72SB on an opposite side of the principal surface 72SA. The intermediate board 73 is flexible. In other words, the wiring board 70 is a rigid flexible wiring board including the rigid boards and the flexible board.

In the image pickup apparatus 1, the second rigid board 72 has a second through hole H70, and the ferrule 40 is inserted in the second through hole H70. An opening of the second through hole H70 is designed according to a shape of the ferrule 40. For example, if the ferrule 40 is a regular hexagonal prism, the opening of the second through hole H70 has a regular hexagonal shape or a circular shape.

The cable 60 has lead wires for transmitting electrical signals to the imager 10 or the optical device 20. The lead wires of the cable 60 are, for example, solder-bonded to electrodes on the back surface 72SB on the opposite side of the principal surface 72SA of the second rigid board 72.

For example, the lead wires of the cable 60 are inserted in a recess on the back surface 72SB and bonded to the electrodes. When the recess is a through hole, the lead wires may be bonded to the principal surface 72SA.

The optical module 30 of the image pickup apparatus 1 is a three-dimensional wiring board in a substantially rectangular parallelepiped in which an angle θ of the first side surface 30SS relative to the first principal surface 30SA is 90 degrees. In the optical module 30, the first side surface 30SS is glued on the principal surface 71SA of the first rigid board 71 with an adhesive 75, and the first principal surface 30SA is mounted on the principal surface 72SA of the second rigid board 72 and bonded with an adhesive 35. Note that a part of the first principal surface 30SA of the optical module 30 is arranged at a position facing the intermediate board 73 and is bonded neither to the second rigid board 72 nor to the intermediate board 73.

In the image pickup apparatus 1, an angle θ formed by the first rigid board 71 and the second rigid board 72 is defined as 90 degrees by the optical module 30 that is a three-dimensional wiring board. In other words, the optical axis O1 along which image pickup light is incident and the optical axis O2 of an optical signal outputted by the optical device 20 (the extension direction of the optical fiber 50) are parallel with each other. In other words, though the image pickup apparatus 1 is small-sized, the optical axis O1 and the optical axis O2 can be easily arranged in parallel.

<Manufacturing Method of Image Pickup Apparatus>

Figure 6:
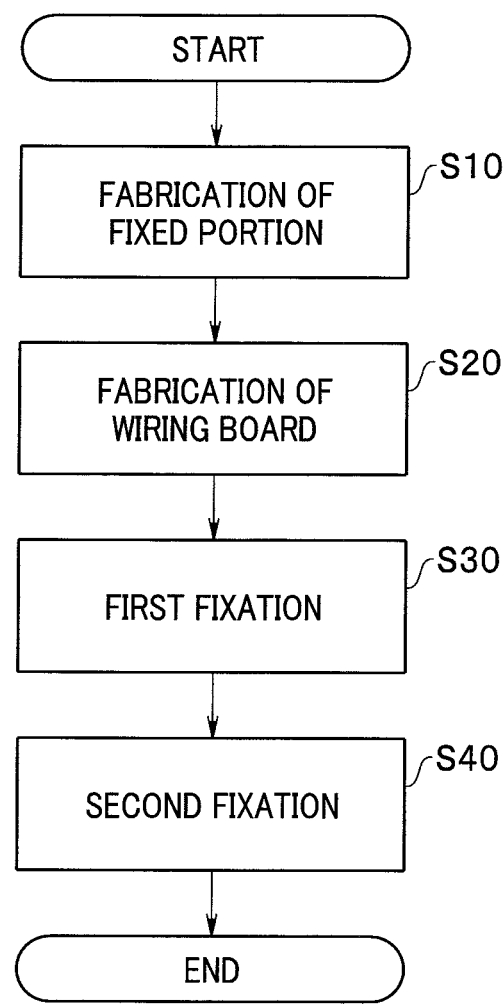
FIG. 6 is a flowchart of a manufacturing method of the image pickup apparatus of the first embodiment.

Next, a manufacturing method of the image pickup apparatus 1 will be described along a flowchart shown in FIG. 6.

<Step S10> Optical Module Fabrication Process

As already described, the optical module 30 is a three-dimensional wiring board that includes the first substrate 31, the second substrate 32 and the third substrate 33 and has wires not shown. Further, each of the second substrate 32 and the third substrate 33 is also a three-dimensional substrate that includes a flat board area and a frame area.

The first substrate 31 has a through wiring (not shown) that connects the first principal surface 30SA and the back surface 31SB on the opposite side of the first principal surface 30SA, and electrodes 38 that are electrically connected to the second substrate 32, the third substrate and the optical device 20 is disposed on the first principal surface 30SA.

On the back surface 31SB of the first substrate 31, the optical device 20 is mounted at a position at which the light emitting portion 21 faces the first through hole H30. The electronic parts 39 are mounted respectively on the second substrate 32 and the third substrate 33. The optical module 30 is fabricated by solder bonding, ultrasonic bonding or ultrasonic thermal bonding the first substrate 31, the second substrate 32 and the third substrate 33.

As a total of the thicknesses of the first substrate 31, the second substrate 32, and the third substrate 33, that is, a length of the optical module 30 in a direction of the optical axis O1 is preferably 1000 μm or more, and more preferably 2500 μm or more, so as to define the angle θ in a stable state.

Note that at least a part of the optical module 30 may be configured with an MID (molded interconnect device) the base material of which is non-conductive resin and which has wires (not shown), electrodes and the like.

Note that, if the thickness of the first substrate 31 is large, a length of the first through hole H30 serving as an optical path is long, and there is a possibility that transmission efficiency decreases. Therefore, it is preferred that the thickness of the first substrate 31 is 30 μm or less. On the other hand, if the thickness of the first substrate 31 is sufficiently large, and it is possible to define the angle θ formed by the first rigid board 71 and the second rigid board 72 as 90 degrees by bonding the side surface 31SS to the principal surface 71SA of the first rigid board 71, then the optical module 30 may have only the first substrate 31. For example, the first substrate 31 may include a flat board area having the first through hole H30 and a frame area constituting the side surface 31SS. Note that, if the first substrate 31 is a transparent substrate, the first through hole H30 is not required.

<Step S20> Wiring Board Fabrication Process

The imager 10 and the wiring board 70 are fabricated. Then, the imager 10 is mounted on the principal surface 71SA of the first rigid board 71 of the wiring board 70. In other words, the bonded electrodes 13 on the back surface 10SB of the imager 10 are bonded to electrodes 74 on the principal surface 71SA. The electrodes 12 on the light receiving surface 10SA of the imager 10 and the electrodes on the principal surface 71SA may be connected by bonding wires. The imager 10 may be either a front-illuminated image sensor or a back-illuminated image sensor.

The wiring board 70 is a rigid flexible wiring board configured with the flexible intermediate board 73 being disposed between the first rigid board 71 and the second rigid board 72. Bases of the first rigid board 71 and the second rigid board 72 are configured with non-flexible boards such as resin boards, ceramic boards, glass epoxy boards, glass boards or silicon boards. The intermediate board 73 has a board configured with a flexible insulator, for example, a polyimide and wires.

Note that the intermediate board 73 may be formed by removing a part of non-flexible boards from a wiring board which is a stack of the non-flexible boards and a flexible board. For example, the flexible intermediate board 73 is formed by removing, from a wiring board where a flexible wiring layer including an insulating layer of polyimide or the like is disposed on a non-flexible ceramic board, a part of the ceramic board.

Though the wiring board 70 is a double-sided wiring board, the wiring board 70 may be a single-sided wiring board or a multi-layer wiring board. Each of the first rigid board 71 and the second rigid board 72 may be a wiring board with built-in electronic parts such as a chip capacitor.

<Step S30> First Fixation Process

The ferrule 40 is disposed at a position where the first through hole H30 of the first principal surface 30SA of the first substrate 31 of the optical module 30 faces the insertion hole H40. Then, as shown in FIG. 7, the ferrule 40 is inserted into the second through hole H70 of the second rigid board 72 of the wiring board 70.

The first principal surface 30SA of the optical module 30 is glued to the principal surface 72SA of the second rigid board 72 with the adhesive 35, and the electrodes 38 on the first principal surface 30SA are bonded to the electrodes (not shown) on the principal surface 72SA of the second rigid board 72. The adhesive 35 may be injected into the bonded portion after the electrodes are bonded. The electrodes on the principal surface 72SA of the second rigid board 72 are connected to the electrodes on the back surface 72SB on the opposite side of the principal surface 72SA via through wires, though not shown.

Figure 7:
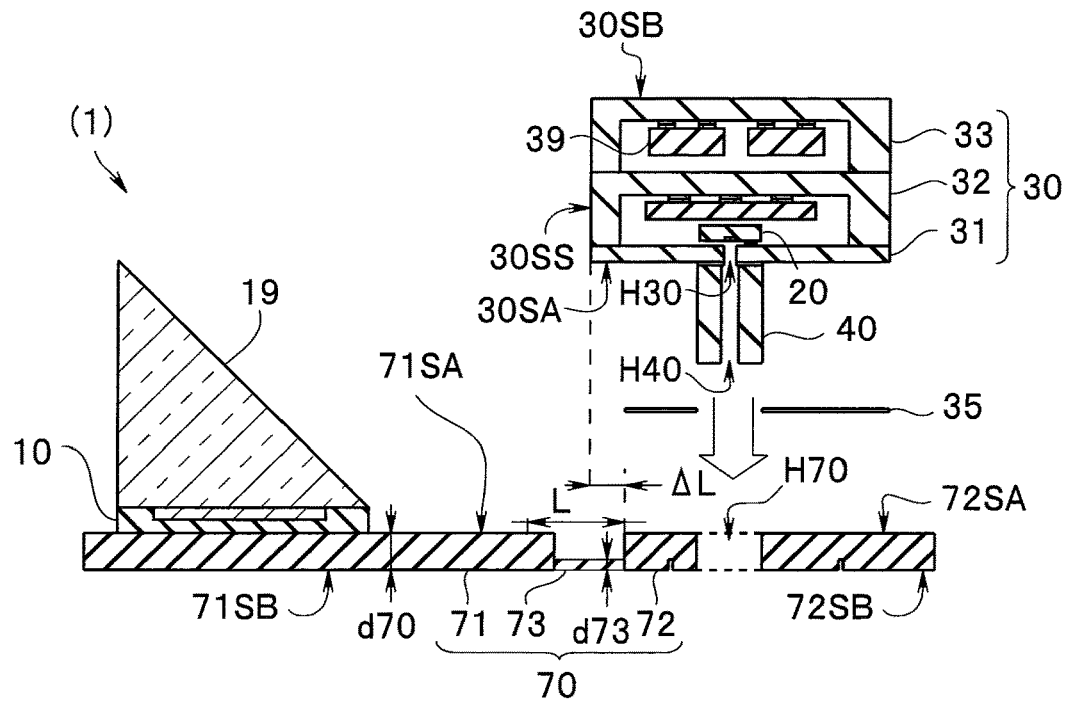
FIG. 7 is a sectional view for describing the manufacturing method of the image pickup apparatus of the first embodiment.

Here, as shown in FIG. 7, the first principal surface 30SA of the optical module 30 is arranged and glued so as to protrude in a direction of the intermediate board 73 from an end surface of the principal surface 72SA of the second rigid board 72 by a length of ΔL. In other words, a part of the first principal surface 30SA is arranged at a position facing the intermediate board 73, and is glued neither to the second rigid board 72 nor to the intermediate board 73. In other words, apart of the optical module 30 protrudes from the second rigid board 72.

There is a possibility that, if the intermediate board 73 excessively deforms when being bent, wires may be damaged. However, the part of the first principal surface 30SA is arranged at the position facing the intermediate board 73 and is glued neither to the second rigid board 72 nor to the intermediate board 73. In other words, a thickness d73 of the intermediate board 73 is thinner than a thickness d70 of the first rigid board 71 and the second rigid board 72, and the intermediate board 73 is arranged neither on an extension line of the principal surface 71SA of the first rigid board 71 nor on an extension line of the principal surface 72SA of the second rigid board 72. Therefore, it is possible to reduce the possibility that the wires are damaged by the intermediate board 73 excessively deforming when being bent.

<Step S40> Second Fixation Process

Figure 8:
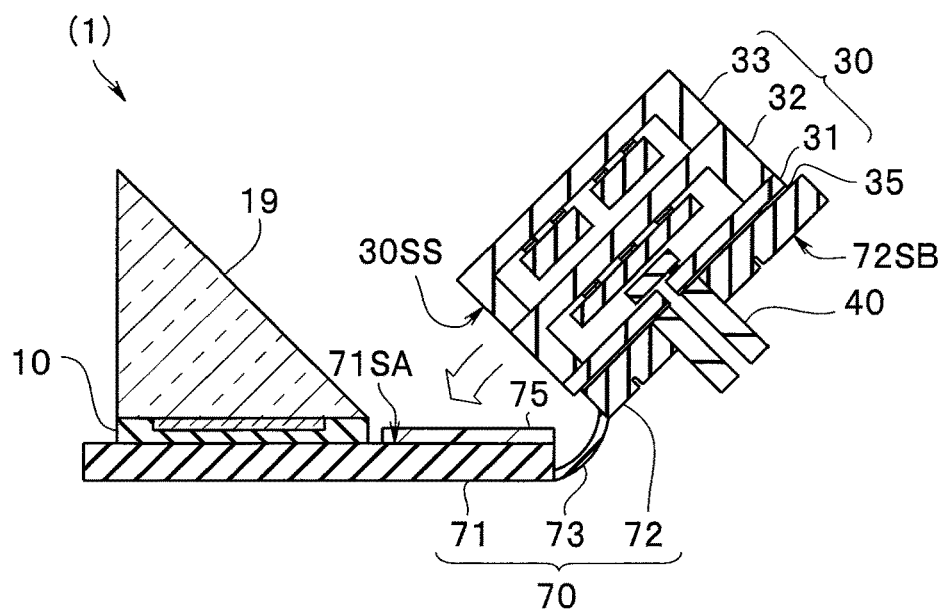
FIG. 8 is a sectional view for describing the manufacturing method of the image pickup apparatus of the first embodiment.

As shown in FIG. 8, the first side surface 30SS of the optical module 30 is glued to the principal surface 71SA of the first rigid board 71 with the adhesive 75 while the intermediate board 73 of the wiring board 70 is being bent.

Since the first principal surface 30SA of the optical module 30 protrudes from the end surface of the principal surface 72SA by the length of ΔL the intermediate board 73 does not excessively deform when the intermediate board 73 is bent, and, therefore, there is no possibility that the wires of the intermediate board 73 are damaged. Note that it is preferred that the length ΔL is 50%30% of the length L of the intermediate board 73.

Figure 4:
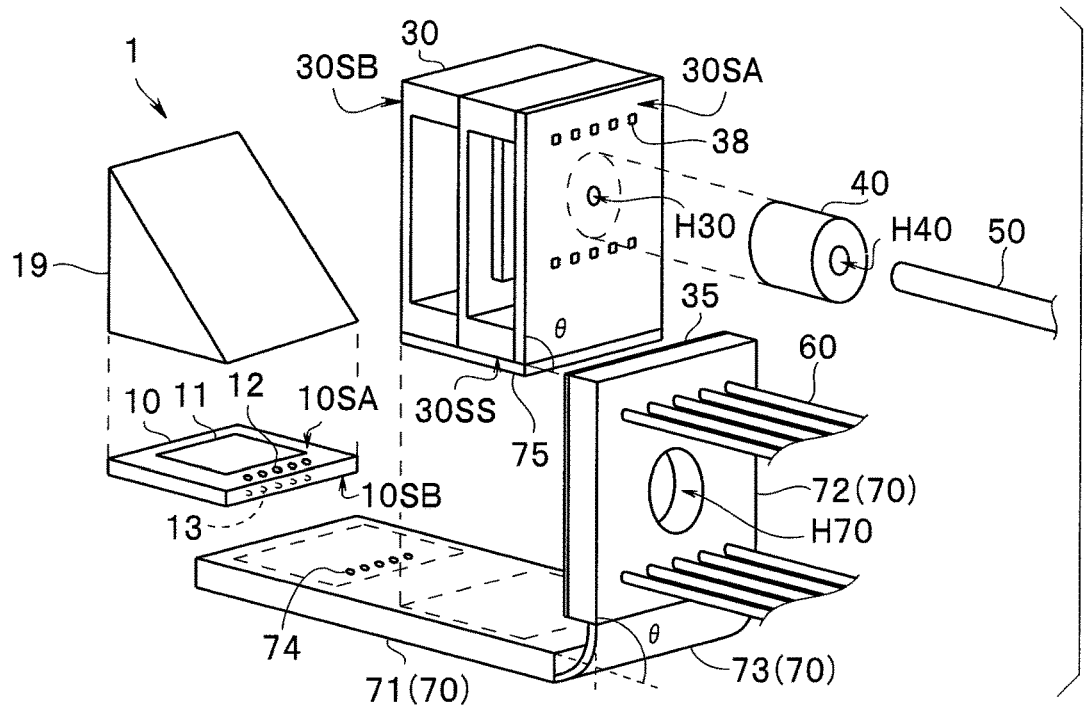
FIG. 4 is an exploded perspective view of the image pickup apparatus of the first embodiment.

The angle θ of the first side surface 30SS of the optical module 30 relative to the first principal surface 30SA is 90 degrees. Therefore, as shown in FIG. 4, by the first side surface 30SS being glued to the first rigid board 71, the angle θ of the first rigid board 71 relative to the second rigid board 72 is automatically defined as 90 degrees.

By the optical fiber 50 being inserted into the insertion hole H40 of the ferrule 40 and the cable 60 being bonded to the electrodes of the back surface 72SB of the second rigid board 72, the image pickup apparatus 1 is completed.

Note that the ferrule 40 may be inserted into the second through hole H70 of the second rigid board 72 after the optical module 30 is glued to the second rigid board 72. Further, the ferrule 40 in which the optical fiber 50 is inserted may be inserted into the second through hole H70.

According to the manufacturing method of the present embodiment, since the angle formed by the first rigid board 71 relative to the second rigid board 72 is accurately a predetermined angle θ (90 degrees), it is possible to easily manufacture the small-sized image pickup apparatus for endoscope 1.

Note that it is preferred that the adhesive 75 is flexible resin with a Young's modulus of 0.1 GPa or less. In other words, though the first principal surface 30SA of the optical module 30 is mounted on the second rigid board 72 of the wiring board 70 by soldering or the like, it is preferred that the side surface 30SS is glued to the first rigid board 71, for example, with silicone resin (with a Young's modulus of 0.05 GPa). A lower limit of the Young's modulus of the adhesive 75 is, for example, 0.005 GPa.

At the time of handling the image pickup apparatus 1 or when the bending portion 90B of the endoscope 9 deforms, a tensile stress may be applied to the optical fiber 50. When the adhesive 75 is flexible resin, there is no possibility that the optical fiber 50 is damaged, because the stress is relieved by the flexible resin elastically deforming due to the applied stress.

The optical module 30 may be covered with flexible resin similar to the adhesive 75. The adhesive 75 may include highly thermally conductive particles.

Modifications of First Embodiment

Since image pickup apparatuses 1A to 1D, endoscopes 9A to 9D having the image pickup apparatuses 1A to 1D and manufacturing methods of the image pickup apparatuses 1A to 1D of modifications of the first embodiment are similar to the image pickup apparatus 1, the endoscope 9 and the manufacturing method of the image pickup apparatus 1 and have the same effects, components having the same functions will be given the same reference signs, and description will be omitted.

Modification 1 of First Embodiment

Figure 9:
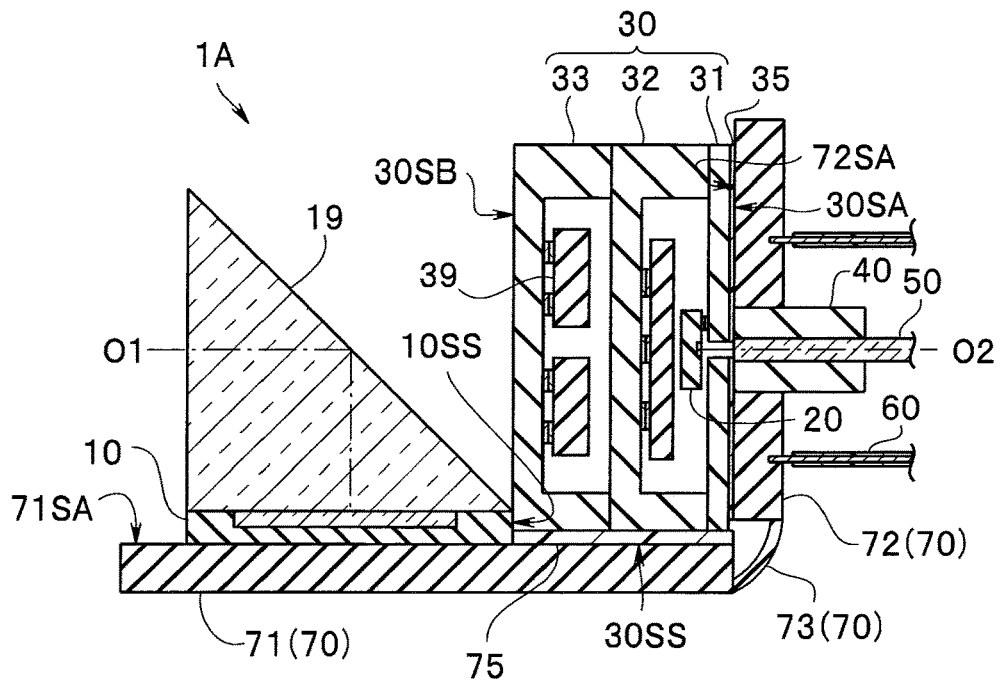
FIG. 9 is a sectional view of an image pickup apparatus of a modification 1 of the first embodiment.

In the image pickup apparatus 1A of the present modification shown in FIG. 9, the second principal surface 30SB of the optical module 30 is in contact with the imager side surface 10SS of the imager 10.

Since positioning of the principal surface 71SA in an in-plane direction is easy at the time of gluing the optical module 30 to the first rigid board 71, the image pickup apparatus 1A is easier to manufacture than the image pickup apparatus 1.

Note that the first side surface 30SS of the optical module 30 and the principal surface 71SA of the first rigid board 71 may have a protrusion and a recess, respectively, so that the optical module 30 may be positioned by the protrusion and the recess being fitted with each other. On the contrary, the first side surface 30SS and the principal surface 71SA of the first rigid board 71 may have a recess and a protrusion, respectively.

Modification 2 of First Embodiment

Figure 10:
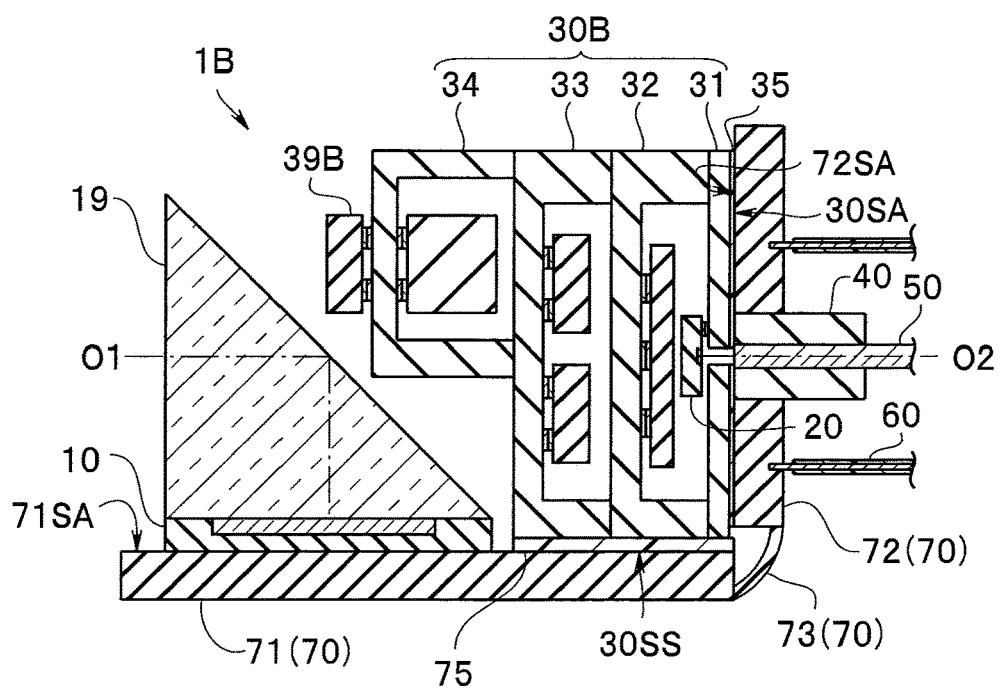
FIG. 10 is a sectional view of an image pickup apparatus of a modification 2 of the first embodiment.

In the image pickup apparatus 1B of the present modification shown in FIG. 10, the right-angle prism 19 is glued to an upper surface of the imager 10 disposed on the first rigid board 71, and a part 34 of an optical module 30B is accommodated in a space above the imager 10 where the right-angle prism 19 is not disposed. Note that an electronic part 39B is mounted on the second principal surface 30SB of the optical module 30B. The electronic part 39B mounted on the second principal surface 30SB is also regarded as a part of the optical module 30B.

Though a lot of electronic parts 39 and 39B are mounted on the optical module 30B in the image pickup apparatus 1B, a length of the image pickup apparatus 1B in an optical axis direction is short because the part 34 (39B) of the optical module 30B is accommodated in the space above the imager 10.

Modification 3 of First Embodiment

Figure 11:
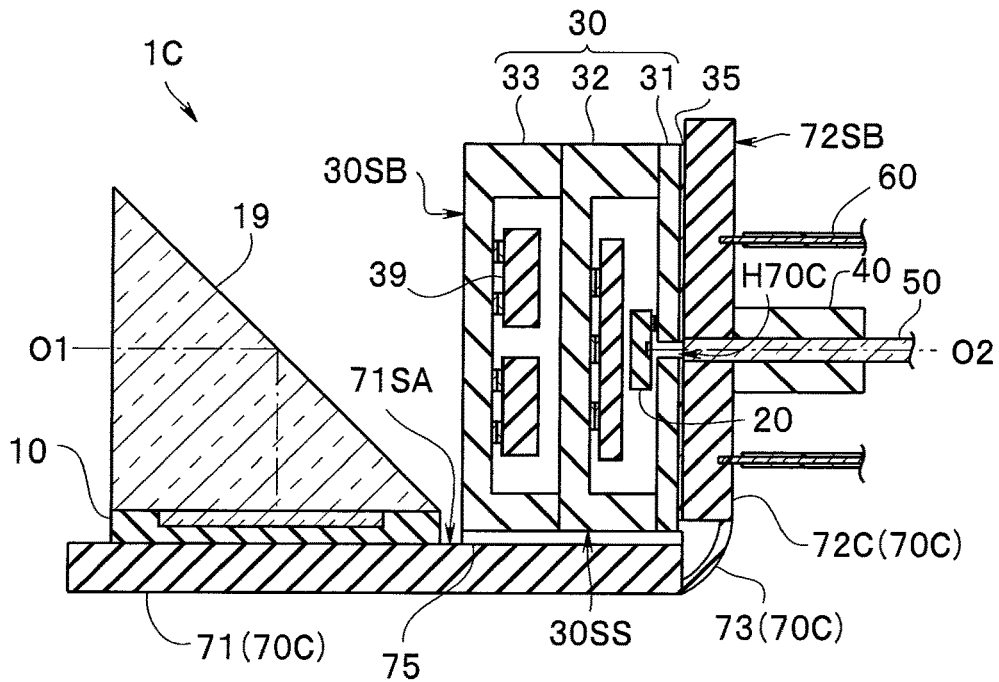
FIG. 11 is a sectional view of an image pickup apparatus of a modification 3 of the first embodiment.

In the image pickup apparatus 1C of the present modification shown in FIG. 11, the ferrule 40 is disposed on the back surface 72SB of the second rigid board 72C of the wiring board 70C, and only the optical fiber 50 is inserted through a second through hole H70C of the second rigid board 72C.

In other words, though the ferrule 40 is inserted through the second through hole H70 of the second rigid board 72C in the image pickup apparatus 1 and the like, only the optical fiber 50 may be inserted through the second through hole H70C.

<Modification 4 of First Embodiment

Figure 12:
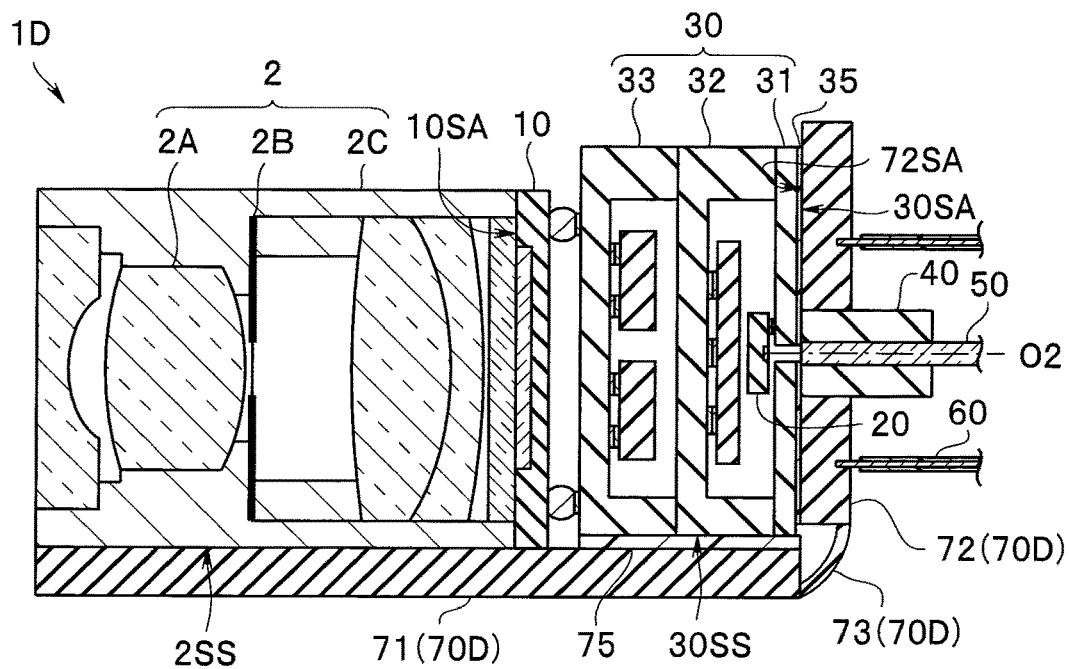
FIG. 12 is a sectional view of an image pickup apparatus of a modification 4 of the first embodiment.

In the image pickup apparatus 1D of the present modification shown in FIG. 12, an image pickup optical system 2 is glued to the light receiving surface 10SA of the imager 10. The image pickup apparatus JD is of a so-called vertical type in which the light receiving surface 10SA of the imager 10 is orthogonal to the optical axis O1 of the image pickup optical system 2.

In the image pickup optical system 2, a plurality of lenses 2A, an optical aperture 2B and the like are accommodated in a lens barrel portion 2C. The image pickup optical system 2 to which the imager 10 is glued is disposed on the first rigid board 71 of a wiring board 70D.

Note that, when the image pickup optical system 2 is fabricated by cutting a stack of optical wafers each of which has a plurality of optical members, the image pickup optical system 2 is in a substantially rectangular parallelepiped. In this case, the angle θ of the second rigid board 72 relative to the first rigid board 71 may be defined by, after bonding the image pickup optical system 2, the imager 10 and the optical module 30, fixing the image pickup optical system 2, the imager 10 and the optical module 30 to the second rigid board 72, and gluing at least either the side surface 2SS of the lens barrel portion 2C or the optical module 30 to a principal surface 71SA of the first rigid board 71. In other words, the lens barrel portion 2C may have functions of the optical module.

Since the image pickup optical system 2 is longer than the optical module 30 in length in the optical axis direction, the angle θ can be more easily and more stably defined than in the case of using only the optical module 30 as an angle definition member.

Second Embodiment

Since an image pickup apparatus 1E of a second embodiment and an image pickup apparatus 1F of a modification of the second embodiment are similar to the image pickup apparatuses 1, and 1A to 1D and have the same effects, components having the same functions will be given the same reference signs, and description will be omitted.

Figure 13:
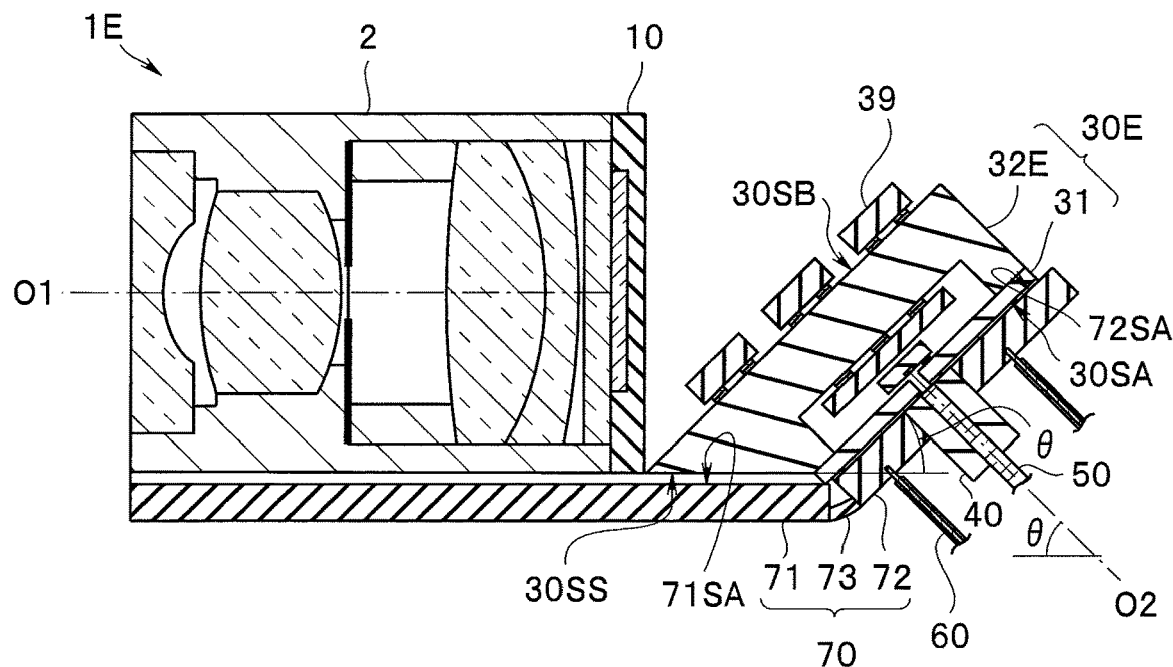
FIG. 13 is a sectional view of an image pickup apparatus of a second embodiment.

In the image pickup apparatus 1E of the present embodiment shown in FIG. 13, a predetermined angle θ of a tilt of the side surface 30SS of an optical module 30E relative to the first principal surface 30SA is 45 degrees. Therefore, the angle θ of the first rigid board 71 relative to the second rigid board 72 is also 45 degrees. The optical fiber 50 is extended in a direction of the angle θ (45 degrees) relative to the optical axis O1 of the image pickup optical system 2.

Figure 14:
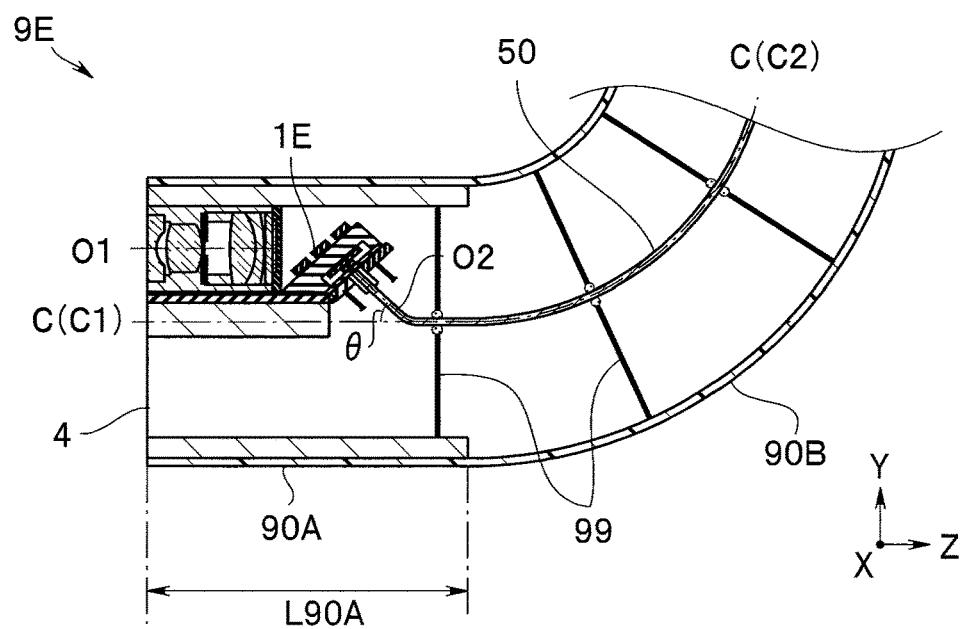
FIG. 14 is a sectional view of a distal end portion of an endoscope of the second embodiment.

As shown in FIG. 14, in an endoscope 9E, the image pickup apparatus 1E is accommodated in a through hole of a casing 4 of the distal end portion 90A with a length L90A. The image pickup apparatus 1E is arranged such that the optical axis O1 is parallel to and eccentric from a distal end portion central axis C1 of the distal end portion 90A.

The optical fiber 50 of the image pickup apparatus 1E is extended toward the distal end portion central axis C1 of the distal end portion 90A and is, in the bending portion 90B, arranged along a bending portion central axis C2 of the bending portion 90B.

In the proximal end portion of the distal end portion 90A and the bending portion 90B, a plurality of guide members 99 are disposed which are configured to arrange the optical fiber 50 along the distal end portion central axis C1 (a central axis C) and the bending portion central axis C2. Details of the guide members 99 are disclosed in Japanese Patent Application Laid-Open Publication No. 2015-97589. It is preferred that the guide members 99 are also disposed in the flexible portion 90C, though it is not shown. Note that, since the flexible portion 90C does not significantly deform in comparison with the bending portion 90B, arrangement intervals among the guide members 99 in the flexible portion 90C may be longer than the arrangement intervals in the bending portion 90B.

As a guide member, one multi-lumen tube which has an outer diameter that is almost equal to an inner diameter of the bending portion 90B and which is inserted in the bending portion 90B may be used. In other words, by inserting the optical fiber 50 in a pipeline that is inserted through a center of the multi-lumen tube, the optical fiber 50 can be arranged along the bending portion central axis C2.

When the insertion portion 90 deforms, a stress is applied to the optical fiber 50 that is inserted in the insertion portion 90 of the endoscope 9E. It is especially when the bending portion 90B deforms by a bending operation that the optical fiber 50 receives a great stress.

In the endoscope 9E, since the optical fiber 50 is arranged along the bending portion central axis C2 of the bending portion 90B, the optical fiber 50 does not receive a great stress even if the bending portion 90B deforms. Therefore, there is no possibility that the optical fiber 50 is damaged, and the endoscope 9E is highly reliable.

In the image pickup apparatus 1E of the endoscope 9E, the optical fiber 50 is arranged such that a fiber distal end portion is tilted at 45 degrees±10 degrees, the 45 degrees being the predetermined angle θ, that is, tilted at an angle of 35 degrees or more and 55 degrees or less relative to the distal end portion central axis C1, on a section (a YZ surface) that includes the distal end portion central axis C and an optical axis O, and an extension direction is toward the distal end portion central axis C1.

Since the optical fiber 50 can be arranged along the bending portion central axis C2 of the bending portion 90B without bending the optical fiber 50 much, the endoscope 9E is highly reliable. Furthermore, since the optical fiber 50 can be arranged along the bending portion central axis C2 of the bending portion 90B at a short distance, the length L90A of the distal end portion 90A is short, and the endoscope 9E is minimally invasive.

The endoscope 9E is an endoscope in which an image pickup apparatus for endoscope is disposed in a distal end portion of an insertion portion, the insertion portion being configured with the distal end portion, a bending portion and a flexible portion that are continuously provided. The image pickup apparatus for endoscope includes: an imager configured to output an image pickup signal; an optical device configured to convert the image pickup signal into an optical signal; an optical module on which the optical device is mounted, the optical module including a first principal surface, a second principal surface on an opposite side of the first principal surface and a first side surface, an angle of the first side surface relative to the first principal surface being a predetermined angle; an optical fiber configured to transmit the optical signal and configured to be optically coupled with the optical device; a ferrule having an insertion hole into which the optical fiber is inserted; and a wiring board including a first rigid board, a second rigid board, and a flexible intermediate board connecting the first rigid board and the second rigid board. The ferrule is fixed to the second rigid board or the first principal surface of the optical module, and the first side surface of the optical module is glued to the first rigid board, and the first principal surface is glued to the second rigid board. The predetermined angle is more than 35 degrees and less than 55 degrees, and an optical axis is parallel to and eccentric from a distal end portion central axis of the distal end portion, and the optical fiber is extended toward the distal end portion central axis and is arranged along a bending portion central axis in the bending portion.

Modification of Second Embodiment

Figure 15:
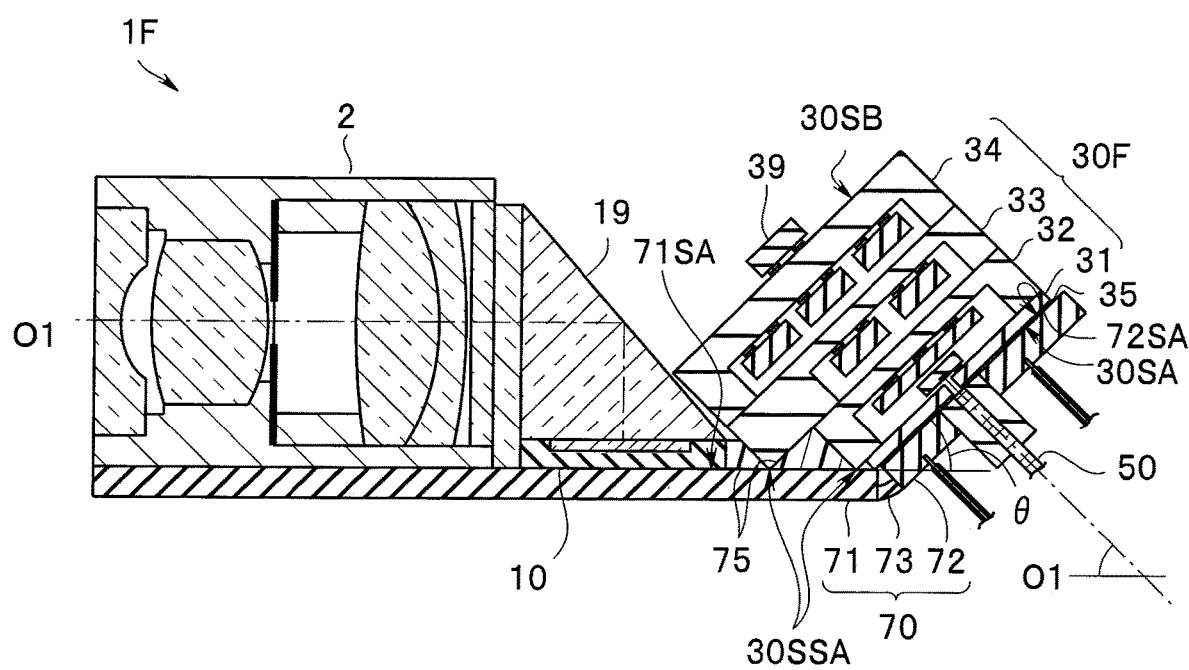
FIG. 15 is a sectional view of an image pickup apparatus of a modification 1 of the second embodiment.

In the image pickup apparatus 1F of the present modification shown in FIG. 15, two corner portions 30SSA on a side surface of an optical module 30F are in contact with the first rigid board 71.

In other words, in the present embodiment, if the angle between the first rigid board 71 and the second rigid board 72 can be defined, it is only necessary that only parts of two or more side surfaces of the optical module are in contact with the first rigid board. Further, in the optical module having a plurality of substrates 31 to 34, the angle between the first rigid board 71 and the second rigid board 72 can be defined if at least a side surface of any of the substrates is in contact with the first rigid board.

In other words, it is only necessary that the optical module has the plurality of substrates 31 to 34 including the first substrate 31 on which the optical device 20 is mounted, and a first side surface that is in contact with the first rigid board 71 is configured with at least the side surface of any of the plurality of substrates 31 to 34.

Note that it goes without saying that the endoscopes 9A to 9F provided with the image pickup apparatuses 1A to 1F have the effects of the endoscope 9 and further have the effects of the image pickup apparatuses 1A to 1F. Though the endoscope 9 is a flexible endoscope, the endoscope 9 may be a rigid endoscope. Further, the endoscopes of the embodiments may be either medical endoscopes or industrial endoscopes.

The present invention is not limited to the embodiments or modifications described above, but various changes, combinations and applications are possible within a range not departing from the spirit of the invention.

What is claimed is:

1. An image pickup apparatus for endoscope, comprising:
   an image sensor configured to output an image pickup signal;
   a light source configured to output the image pickup signal into as an optical signal;
   an optical module on which the light source is mounted, the optical module comprising a first principal surface, a second principal surface on an opposite side of the first principal surface, and a first side surface, an angle of the first side surface relative to the first principal surface being a predetermined angle;

an optical fiber configured to transmit the optical signal and configured to be optically coupled with the light source;

a ferrule having an insertion hole into which the optical fiber is inserted; and a wiring board comprising a first rigid board, a second rigid board, and a flexible intermediate board connecting the first rigid board and the second rigid board, wherein the ferrule is fixed to the second rigid board or the first principal surface of the optical module;

the first side surface of the optical module is glued to the first rigid board, and the first principal surface is glued to the second rigid board;

a right-angle prism is glued to an upper surface of the image sensor disposed on the first rigid board; and a part of the optical module is accommodated in a space above the image sensor where the right-angle prism is not disposed.

2. The image pickup apparatus for endoscope according to claim 1, wherein a part of the first principal surface is arranged at a position facing the intermediate board.

3. The image pickup apparatus for endoscope according to claim 1, wherein the optical module comprises a plurality of substrates including a first substrate on which the light source is mounted, and the first side surface is configured with at least any of side surfaces of the plurality of substrates.

4. The image pickup apparatus for endoscope according to claim 3, wherein at least any of the plurality of substrates is a three-dimensional substrate including a flat board area and a frame area.

5. The image pickup apparatus for endoscope according to claim 1, wherein the wiring board is a rigid flexible wiring board the intermediate board of which is configured with a flexible wiring board.

6. The image pickup apparatus for endoscope according to claim 1, wherein a Young's modulus of an adhesive with which the first side surface and the first rigid board are glued is 0.1 GPa or less.

7. The image pickup apparatus for endoscope according to claim 1, wherein the image sensor is disposed on the first rigid board, and the second principal surface of the optical module is in contact with an image sensor side surface of the image sensor.

8. The image pickup apparatus for endoscope according to claim 1, wherein the ferrule is inserted through a through hole of the second rigid board.

9. The image pickup apparatus for endoscope according to claim 1, wherein the predetermined angle is 90 degrees.

10. An endoscope comprising:
an image pickup apparatus for endoscope, the image pickup apparatus for endoscope comprising:
an image sensor configured to output an image pickup signal;
a light source configured to output the image pickup signal as an optical signal;
an optical module on which the light source is mounted, the optical module comprising a first principal surface, a second principal surface on an opposite side of the first principal surface, and a first side surface, an angle of the first side surface relative to the first principal surface being a predetermined angle;
an optical fiber configured to transmit the optical signal and configured to be optically coupled with the light source;
a ferrule having an insertion hole into which the optical fiber is inserted; and
a wiring board comprising a first rigid board, a second rigid board, and a flexible intermediate board connecting the first rigid board and the second rigid board,
wherein the ferrule is fixed to the second rigid board or the first principal surface of the optical module;
the first side surface of the optical module is glued to the first rigid board, and the first principal surface is glued to the second rigid board;
a right-angle prism is glued to an upper surface of the image sensor disposed on the first rigid board; and
a part of the optical module is accommodated in a space above the image sensor where the right-angle prism is not disposed.

11. A manufacturing method of an image pickup apparatus for endoscope, the image pickup apparatus for endoscope comprising:
an image sensor configured to output an image pickup signal;
a light source configured to output the image pickup signal as an optical signal;
an optical module on which the light source is mounted, the optical module comprising a first principal surface, a second principal surface on an opposite side of the first principal surface, and a first side surface, an angle of the first side surface relative to the first principal surface being a predetermined angle;
an optical fiber configured to transmit the optical signal and configured to be optically coupled with the light source;
a ferrule having an insertion hole into which the optical fiber is inserted; and
a wiring board comprising a first rigid board, a second rigid board and a flexible intermediate board connecting the first rigid board and the second rigid board;
wherein the ferrule is fixed to the second rigid board or the first principal surface of the optical module;
the first side surface of the optical module is glued to the first rigid board, and the first principal surface is glued to the second rigid board,
a right-angle prism is glued to an upper surface of the image sensor disposed on the first rigid board; and
a part of the optical module is accommodated in a space above the image sensor where the right-angle prism is not disposed
the method comprising:
gluing the first principal surface of the optical module to the second rigid board; and
bending the intermediate board and gluing the side surface of the optical module to the first rigid board.

12. The manufacturing method of the image pickup apparatus for endoscope according to claim 11, wherein, when the optical module is glued to the second rigid board, a part of the first principal surface of the optical module is arranged at a position facing the flexible intermediate board.

* * * * *